(12) United States Patent
Okoshi et al.

(10) Patent No.: US 9,815,807 B2
(45) Date of Patent: Nov. 14, 2017

(54) METHOD FOR PRODUCING 2-FURALDEHYDE

(71) Applicant: MITSUBISHI CHEMICAL CORPORATION, Chiyoda-ku (JP)

(72) Inventors: Toru Okoshi, Kanagawa (JP); Hideto Tsuji, Kanagawa (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 0 days.

(21) Appl. No.: 15/194,210

(22) Filed: Jun. 27, 2016

(65) Prior Publication Data

US 2016/0304482 A1 Oct. 20, 2016

Related U.S. Application Data

(63) Continuation of application No. 13/953,191, filed on Jul. 29, 2013, now Pat. No. 9,403,787, which is a continuation of application No. PCT/JP2012/051701, filed on Jan. 26, 2012.

(30) Foreign Application Priority Data

Jan. 28, 2011 (JP) .................................. 2011-016943

(51) Int. Cl.

| | | |
|---|---|---|
| C07D 307/50 | (2006.01) | |
| B01J 23/30 | (2006.01) | |
| B01J 21/06 | (2006.01) | |
| B01J 21/08 | (2006.01) | |
| B01J 21/12 | (2006.01) | |
| B01J 21/16 | (2006.01) | |
| B01J 23/14 | (2006.01) | |
| B01J 27/185 | (2006.01) | |
| B01J 27/053 | (2006.01) | |
| B01J 29/70 | (2006.01) | |
| B01J 29/08 | (2006.01) | |
| B01J 21/04 | (2006.01) | |
| B01J 27/16 | (2006.01) | |
| B01J 27/18 | (2006.01) | |
| B01J 27/182 | (2006.01) | |

(52) U.S. Cl.
CPC ............ *C07D 307/50* (2013.01); *B01J 21/04* (2013.01); *B01J 21/063* (2013.01); *B01J 21/066* (2013.01); *B01J 21/08* (2013.01); *B01J 21/12* (2013.01); *B01J 21/16* (2013.01); *B01J 23/14* (2013.01); *B01J 23/30* (2013.01); *B01J 27/053* (2013.01); *B01J 27/16* (2013.01); *B01J 27/18* (2013.01); *B01J 27/182* (2013.01); *B01J 27/1853* (2013.01); *B01J 29/084* (2013.01); *B01J 29/7007* (2013.01)

(58) Field of Classification Search
CPC ... C07D 307/50; B01J 29/084; B01J 29/7007; B01J 27/182; B01J 27/18; B01J 27/16; B01J 27/053; B01J 23/30; B01J 27/1853; B01J 21/16; B01J 21/12; B01J 21/08; B01J 21/066; B01J 21/063; B01J 23/14; B01J 21/04
See application file for complete search history.

(56) References Cited

U.S. PATENT DOCUMENTS

| | | | |
|---|---|---|---|
| 2010/0083565 A1 | 4/2010 | Gruter | |
| 2013/0172584 A1* | 7/2013 | Corbin | ................. C07D 307/50 549/489 |

FOREIGN PATENT DOCUMENTS

| | | |
|---|---|---|
| JP | 10-204075 | 8/1998 |
| JP | 10-265468 | 10/1998 |
| JP | 2002-205970 | 7/2002 |
| JP | 2002205970 A | 7/2002 |
| JP | 2010-538033 | 12/2010 |
| JP | 5779888 B2 | 9/2015 |
| SU | 1659763 * | 5/1971 |
| WO | WO 97/02233 | 1/1997 |
| WO | WO 98/17727 A1 | 4/1998 |
| WO | WO 2007/146636 A1 | 12/2007 |
| WO | 2009/030511 | 3/2009 |
| WO | WO 2009030511 | 3/2009 |
| WO | 2010/101024 | 9/2010 |
| WO | WO 2010/124381 A1 | 11/2010 |
| WO | WO 2011/000030 A1 | 1/2011 |
| WO | WO2012038968 | 3/2012 |

OTHER PUBLICATIONS

SU-1659763 ProQuest English machine translation and appended Derwent record p. 1-10.*
International Search Report dated Feb. 28, 2012 in PCT/JP2012/051701 filed Jan. 26, 2012.
"Synthesis of furfurals from monosaccharides using solid acid and base catalysts", Gekkan fine chemical, 2010, vol. 39, No. 6, pp. 28-35.
Bir Sain, et al, "Furfural and Furfural-based Industrial Chemicals", Journal of Scientific and Industrial Research, vol. 41 (1982), p. 431-438.
Karl J. Zeitsch, "Furfural production needs", Chemical Innovation, Apr. (2000), p. 29-32.
Avelino Corma, et al. "Chemical Routes for the Transformation of Biomass into Chemicals", Chem. Rev. 2007, 107, p. 2411-2502.
Haruo Kawamoto, et al. "Catalytic pyrolysis of cellulose in sulfolane with some acidic catalysts", Journal of Wood Science, 53(2007), p. 127-133.

(Continued)

*Primary Examiner* — Matt Mauro
(74) *Attorney, Agent, or Firm* — Oblon, McClelland, Maier & Neustadt, L.L.P.

(57) ABSTRACT

An object of the present invention is to provide a method for suppressing the corrosion of a reactor and reducing waste in the production of 2-furaldehyde from a sugar raw material containing a hexose as a constituent component, and another object of the invention is to provide an industrially advantageous method for producing 2-furaldehyde, which suppresses a decrease in the activity of a catalyst in a case of using an acid catalyst and provides a higher yield. The present invention relates to a method for producing 2-furaldehyde comprising heating a sugar raw material containing a hexose as a constituent component in an aprotic polar solvent in the presence of a solid acid catalyst.

11 Claims, No Drawings

(56) References Cited

OTHER PUBLICATIONS

Extended European Search Report dated Jun. 20, 2014, in the corresponding European patent application.
Haruo Kawamoto, et al., "Inhibition of acid-catalyzed depolymerization of cellulose with boric acid in non-aqueous acidic media", Carbohydrate Research 343 (2008) 249-255, Received Oct. 6, 2007; accepted Nov. 1, 2007, Available online Nov. 7, 2007.
Atsushi Takagaki, "One-pot Formation of Furfural from Xylose via Isomerization and Successive Dehydration Reactions over Heterogeneous Acid and Base Catalysts", (Received Apr. 21, 2010; CL-100386; E-mail: ebitani@jaist.ac.jp), Published on the web Jul. 3, 2010.
Office Action dated May 19, 2015 in European Patent Application No. 12 739 294.2.
Japanese Office Action dated Jun. 30, 2015, in corresponding Japanese Patent Application No. 2012-554842 (with English-language Translation).
Moffat, J. B. "Phosphates as catalysts." Catalysis Reviews Science and Engineering 18.2 (1978): 199-258.
Vetrivel, R. "Acid-base properties of H3PO4 and phosphate catalysts." Surface technology 22.1 (1984): 1-8.
Kawamoto JP2002-205970 A English Machine Translation Feb. 25, 2014.
Moreau, C "Dehydration of fructose to 5-hydroxymethylfurfural over H-mordenites." Applied Catalysis A: General 145.1 (1996): 211-224.
Montane, D. "High-temperature dilute-acid hydrolysis of olive stones for furfural production." Biomass and Bioenergy 22.4 (2002): 295-304.
Japanese Office Action dated Dec. 13, 2016 in Patent Application No. 2016-028651(with English translation).
Atsushi Takagaki, et al.. "One-pot Formation of Furfural from Xylose Via Isomerization and Successive Dehydration Reactions Over Heterogeneous Acid and Base Catalysts" Chemistry Letters, vol. 39, No. 8, 2010, pp. 838-840 and cover page.

* cited by examiner

US 9,815,807 B2

METHOD FOR PRODUCING 2-FURALDEHYDE

CROSS REFERENCE TO RELATED APPLICATION(S)

This application is a continuation of U.S. application Ser. No. 13/953,191, filed on Jul. 29, 2013, which is a continuation application of international patent application PCT/JP2012/051701, filed on Jan. 26, 2012, the text of which is incorporated by reference, and claims foreign priority to JP 2011-016943, filed on Jan. 28, 2011, the entire content of which is incorporated herein by reference.

TECHNICAL FIELD

The present invention relates to a method for producing 2-furaldehyde using a sugar as a raw material.

BACKGROUND ART

2-Furaldehyde is a useful compound which can be used as a raw material for producing furan, tetrahydrofuran, a furan resin, etc. 2-Furaldehyde is generally not produced from a raw material derived from petroleum, but is produced using a sugar derived from a plant as a raw material. Therefore, 2-furaldehyde is not classified into a chemical product derived from a petroleum raw material but is classified into a chemical product derived from a plant raw material.

As a method for producing 2-furaldehyde, a method in which a raw material containing a five-carbon sugar such as a pentosan or a pentose is reacted in the presence of an acid catalyst to dehydrate the five-carbon sugar, whereby 2-furaldehyde is obtained has been conventionally known (NPL 1 and NPL 2). Such a five-carbon sugar is contained in hemicellulose, etc. contained in an agricultural waste material such as a sugar cane residue (bagasse) resulted from extraction of juice, corncobs, or wood.

However, the above-described agricultural waste material serving as a representative raw material containing such a five-carbon sugar has a limit to the accumulation of the raw material. Further, the content of hemicellulose in the above-described representative raw material is not so high. For example, the content of hemicellulose in wood is at most about 25%. Due to this, a method for obtaining 2-furaldehyde from a five-carbon sugar has a problem that the yield of 2-furaldehyde per raw material to be used is low. In view of this, there has been a demand for a method for obtaining 2-furaldehyde from a constituent component which exits in a plant more abundantly.

Therefore, attention is paid to cellulose which is a main component of wood and exists abundantly in nature as a natural fiber. Cellulose is a linear polymer containing glucose which is a six-carbon sugar, as a main component. However, since cellulose has high crystallinity, it is difficult to hydrolyze cellulose into a six-carbon sugar serving as a constituent component. Further, it is known that when a six-carbon sugar obtained by hydrolyzing cellulose is reacted in the presence of an acid catalyst to effect dehydration in the same manner as the above-described method for obtaining 2-furaldehyde from a five-carbon sugar, the six-carbon sugar is not inverted into 2-furaldehyde, but inverted into 5-hydroxymethyl-2-furaldehyde (for example, PTL 1 and NPL 3).

On the other hand, a method for producing 2-furaldehyde from a raw material containing a six-carbon sugar is also proposed. Cellulose which is a main component of wood contains glucose which is a six-carbon sugar (a hexose) as a constituent unit. PTL 2 and NPL 4 propose a method for obtaining 2-furaldehyde by heating cellulose in an aprotic polar solvent in the presence of sulfuric acid.

CITATION LIST

Patent Literature

PTL 1: JP-A-10-265468
PTL 2: JP-A-2002-205970

Non Patent Literature

NPL 1: Journal of Scientific and Industrial Research, Vol. 41 (1982), pp. 431-438
NPL 2: Chemical Innovation, April (2000), pp. 29-32
NPL 3: Chem. Rev. 2007, 107, p. 2411
NPL 4: Journal of Wood Science, 53 (2007), pp. 127-133

SUMMARY OF INVENTION

Technical Problem

As described above, in the conventional production of 2-furaldehyde having been already disclosed, heating in the presence of an acid is required in the method in which either a five-carbon sugar or a six-carbon sugar is used as a raw material. Such a method has a problem that a reactor is corroded since an acid to be used in the reaction is dissolved in a solvent. Further, the method also has a problem that it is necessary to dispose of a waste acid after reaction.

Further, although the production reaction of 2-furaldehyde disclosed in the above-described PTL 1 is a batchwise reaction in which 2-furaldehyde is produced by feeding cellulose serving as a raw material at a time to a reaction mixture containing both of an aprotic solvent and sulfuric acid, the present inventors carried out the production reaction as a continuous reaction in which a reaction is performed by continuously adding the raw material and found that the yield of produced 2-furaldehyde decreased as the reaction time increased (Comparative Example 1). Further, such a decrease in the yield was observed in the same manner even when the amount of the catalyst was increased (Comparative Example 2).

This decrease in the activity of the acid catalyst over time is problematic also for the batchwise reaction as a decrease in the yield of the final target product.

Therefore, an object of the present invention is to provide an industrially advantageous method for producing 2-furaldehyde, which suppresses a decrease in the activity of the above-described acid catalyst and provides a higher yield. Further, another object of the invention is to provide a method for suppressing the corrosion of a reactor and reducing waste in the production of 2-furaldehyde from a raw material containing a sugar such as cellulose containing a hexose as a constituent component.

Solution to Problem

The cause of a decrease in the activity of the above-described acid catalyst over time was intensively studied. According to PTL 1 and NPL 4, there is a description that an acid acts on a low-molecular weight compound generated by thermal decomposition of cellulose and the compound is converted into 2-furaldehyde. The present inventors made a hypothesis that when an acid such as sulfuric acid that is uniformly dissolved in a solvent is used, a side reaction such as dehydration or carbonization is promoted by causing the acid to act directly on cellulose, and therefore, the above-described decrease in the activity is observed.

Therefore, when a solid acid catalyst was used in a method for producing 2-furaldehyde in which a raw material containing a sugar such as cellulose containing a hexose as a constituent component is heated in an aprotic polar solvent in the presence of an acid on the basis of the above-described hypothesis, it was found that a decrease in the yield of the target product as in the case of using the above-described acid as the catalyst is not observed. Further, the solid acid catalyst can suppress the corrosion of a reaction vessel, and the acid can be easily separated and collected even after completion of the reaction, and therefore, waste can also be reduced. The present invention was completed by these findings.

That is, the gist of the present invention resides in the following aspects.

(1) A method for producing 2-furaldehyde comprising heating a sugar raw material containing a hexose as a constituent component in an aprotic polar solvent in the presence of a solid acid catalyst.
(2) The method for producing 2-furaldehyde according to the item (1) above, wherein the reaction is performed while discharging produced 2-furaldehyde to the outside of the reaction system.
(3) A method for producing 2-furaldehyde comprising heating a sugar raw material containing a hexose as a constituent component in a solvent in the presence of a solid acid catalyst, wherein the reaction is performed while discharging produced 2-furaldehyde to the outside of the reaction system.
(4) The method for producing 2-furaldehyde according to the item (2) or (3) above, wherein the produced 2-furaldehyde is discharged to the outside of the system in a gas phase.
(5) The method for producing 2-furaldehyde according to any one of the items (2) to (4) above, wherein the solvent has a boiling point higher than 2-furaldehyde.
(6) The method for producing 2-furaldehyde according to any one of the items (2) to (5) above, wherein the reaction temperature is equal to or higher than the boiling point of 2-furaldehyde and equal to or lower than the boiling point of the solvent.
(7) The method for producing 2-furaldehyde according to any one of the items (2) to (6) above, wherein the reaction is performed while discharging 2-furaldehyde to the outside of the reaction system such that the amount of 2-furaldehyde contained in the reaction system is 10% by weight or less with respect to the amount of the solvent.
(8) The method for producing 2-furaldehyde according to any one of the items (1) to (7) above, wherein the heating is performed while supplying water to the reaction system.
(9) The method for producing 2-furaldehyde according to any one of the items (1) to (8) above, wherein the sugar raw material contains cellulose.
(10) The method for producing 2-furaldehyde according to any one of the items (1) to (9) above, wherein the sugar raw material contains a starch.
(11) The method for producing 2-furaldehyde according to any one of the items (1) to (10) above, wherein the sugar raw material contains a hexose.
(12) The method for producing 2-furaldehyde according to any one of the items (1) to (11) above, wherein the solid acid catalyst is a composite oxide.
(13) The method for producing 2-furaldehyde according to the item (12) above, wherein the composite oxide contains two or more elements selected from the group consisting of B, Al, Si, P, Ti, V, Cr, Mn, Fe, Co, Ni, Cu, Zn, Ga, Ge, Y, Zr, Nb, Mo, Sn, a lanthanoid metal, Hf, Ta, and W, and is not uniformly dissolved in the aprotic polar solvent under the reaction conditions.
(14) The method for producing 2-furaldehyde according to the item (12) or (13) above, wherein the composite oxide contains, as constituent components, one or more members selected from the group consisting of B—P, B—P—Al, B—P—Ti, B—P—Si, B—P—Zr, Ti—B, Si—Al, Sn—B, Zr—B, Al—P, Ti—P, Fe—P, Al—W, Al—B, Zr—W, Ti—Zr, Ti—Si, Zn—P, and Sn—P.
(15) The method for producing 2-furaldehyde according to any one of the items (1) to (11) above, wherein the solid acid catalyst is at least one member selected from the group consisting of a metal oxide, a zeolite, and a clay compound.
(16) The method for producing 2-furaldehyde according to any one of the items (1) to (11) above, wherein the solid acid catalyst is a metal sulfate.
(17) The method for producing 2-furaldehyde according to the item (16) above, wherein the metal sulfate is at least one member selected from the group consisting of aluminum sulfate, zirconium sulfate, zinc sulfate, nickel sulfate, and ferric sulfate.

Effects of Invention

According to the present invention, when 2-furaldehyde is produced using, as a sugar raw material, cellulose or the like containing a hexose as a constituent component, a solid acid which is difficult to be soluble in a solvent is used, and therefore, the corrosion of a reaction vessel can be suppressed, and also the acid can be easily separated and collected even after completion of the reaction, and therefore, also waste can be reduced. In addition, a decrease in the activity of the catalyst over time is suppressed, and the reaction yield of finally obtained 2-furaldehyde is improved, and therefore, an industrially advantageous method for producing 2-furaldehyde can be provided.

DESCRIPTION OF EMBODIMENTS

Hereinafter, the present invention will be described in detail, however, the description of the constituent features described below is an example (a representative example) of embodiments of the invention, and the invention is not limited to these contents and can be implemented by variously modifying the embodiments within the scope of the gist thereof.

<Sugar Raw Material Containing Hexose as Constituent Component>

The sugar raw material containing a hexose as a constituent component to be used in the invention refers to a material containing, as its constituent component, a hexose (a six-carbon sugar) in which the number of carbon atoms constituting the sugar is 6.

The way of incorporation of the hexose as a constituent component is not particularly limited, however, the hexose may be incorporated in a sugar molecule or the hexose may be incorporated in a mixture. Further, a natural substance or the like, which can be used as a raw material of a sugar containing a hexose (for example, a polysaccharide such as cellulose described later), is also included.

The hexose contained as a constituent component is not particularly limited, and may be any of an aldose, a ketose, and a deoxy sugar. Specific examples thereof include aldoses such as allose, talose, gulose, glucose (grape sugar), altrose, mannose, galactose, and idose; ketoses such as psicose, fructose (fruit sugar), sorbose, and tagatose; deoxy sugars such as fucose, fuculose, and rhamnose; and the like. Preferably, since the content in the raw material described below is high, glucose and fructose are preferred, and glucose is more preferred due to its availability from a non-edible raw material. Further, the sugar raw material to be used in the invention may contain one hexose or two or more hexoses among the above-described hexoses.

Examples of the sugar raw material containing a hexose as a constituent component in the invention include materials containing a hexose. Specifically, it is a sugar containing a hexose as a constituent component, and specific examples thereof include the above-described hexose monosaccharides; disaccharides containing a hexose such as sucrose (cane sugar), lactose (milk sugar), trehalose, isotrehalose, turanose, cellobiose, kojibiose, sophorose, nigerose, laminaribiose, maltose (malt sugar), isomaltose, and gentiobiose; oligosaccharides containing a hexose such as raffinose, panose, maltotriose, melezitose, gentianose, stachyose, galacto-oligosaccharides, fructo-oligosaccharides, lacto-oligosaccharides, and mannan-oligosaccharides; and polysaccharides containing a hexose such as cellulose, a starch, and a dextrin.

Examples of the sugar raw material containing a hexose as a constituent component in the invention also include, in addition to the above-described materials containing a hexose, materials to be used as raw materials of these sugars, for example, natural substances, and the like.

Specific examples of such a sugar raw material include raw materials containing cellulose such as wood, paper, cotton, rice straws, wheat straws, corncobs, and a sugar cane residue (bagasse) resulted from extraction of juice; raw materials containing a starch such as potatoes (such as Irish potatoes and sweet potatoes), rice, wheat, and corn; fruit juices and molasses containing a plurality of sugars such as fruit juices, starch syrups, and honey; and the like. The above-described raw materials may be used alone or in combination of two or more kinds thereof.

Further, a residue of a raw material containing a pentose and a hexose as constituent components such as wood after extracting and utilizing a five-carbon sugar (pentose) component from the raw material can also be used as the raw material of the invention. It is also effective to use a waste material containing large amounts of ash components and coexisting components such as paper sludge as the raw material.

Among these materials, a material containing cellulose is preferred as the sugar raw material since cellulose exists in a large amount as a main constituent component in a tree or a grass, and also is a non-edible resource unlike a starch or sucrose. Further, a material containing a starch is preferably used since a material with high purity can be easily obtained.

<Aprotic Polar Solvent>

In the method for producing 2-furaldehyde of the invention, the reaction solvent is not particularly limited as long as it fulfills the objects of the invention, however, generally, a solvent capable of allowing a reaction described below to proceed while discharging 2-furaldehyde which is mainly produced by the reaction to the outside of the reaction system, preferably in a gas phase, more preferably a solvent having a boiling point equal to or higher than the boiling point of 2-furaldehyde is used. Specific examples thereof include aprotic polar solvents, ionic liquids, molten salts, and supercritical carbon dioxide.

As the kind of the reaction solvent, an aprotic polar solvent is preferably used. The aprotic polar solvent has low reactivity with the raw material or 2-furaldehyde which is a product, and is stable against a solid acid to be used as the catalyst. The kind of the aprotic polar solvent is not particularly limited as long as it can achieve the objects of the invention, however, an aprotic polar solvent having a boiling point higher than 2-furaldehyde is preferably used from the viewpoint that such a solvent stably functions as a solvent at a reaction temperature. Specific examples thereof include dimethylformamide, N-methyl-2-pyrrolidone, dimethyl sulfoxide, hexamethyl phosphoric triamide, dimethyl sulfone, sulfolane (tetrahydrothiophene-1,1-dioxide), and phthalide (1,3-dihydroisobenzofuran-1-one). From the viewpoint of the yield of 2-furaldehyde, dimethyl sulfone, sulfolane, and phthalide are preferred.

The above-described solvents may be used alone or in combination of two or more kinds thereof. The using amount of the reaction solvent to be used in the invention is not particularly limited as long as it fulfills the objects of the invention. Specifically, the amount of the reaction solvent may be an amount which is sufficient for dissolving an intermediate such as levoglucosan obtained by thermal decomposition of the reaction raw material and does not inhibit the conversion into 2-furaldehyde.

<Solid Acid Catalyst>

In the method for producing 2-furaldehyde of the invention, a solid acid is used as the catalyst. The solid acid catalyst to be used in the invention generally refers to a catalyst which is in the form of a solid and exhibits acidity, and preferably refers to a catalyst which is maintained in the form of a solid even in the reaction solvent or the like, is not uniformly dissolved in the reaction solvent or the like and can exhibit acidity.

The kind of the solid acid catalyst is not particularly limited as long as it can achieve the objects of the invention, however, specific examples thereof include composite oxides, metal oxides, clay compounds, zeolites, and metal sulfates. It is preferred that at least one or more kinds selected from these catalysts are contained from the viewpoint of obtaining catalytic performance.

The composite oxide is not particularly limited, however, a composite oxide containing an element which is converted into an amphoteric oxide or an acidic oxide when it is converted into an oxide, for example, two or more elements selected from B, Al, Si, P, Ti, V, Cr, Mn, Fe, Co, Ni, Cu, Zn, Ga, Ge, Y, Zr, Nb, Mo, Sn, a lanthanoid metal, Hf, Ta, and W is preferred. Preferred examples thereof include composite oxides containing an element having a high valence (of a metal element constituting an oxide) and high covalency such as B, Al, Si, P, Ti, or Zr. Specific examples thereof include composite oxides containing, as constituent elements, B—P, B—P—Al, B—P—Ti, B—P—Si, B—P—Zr, Ti—B, Si-Al, Sn—B, Zr—B, Al—P, Ti—P, Fe—P, Al—W, Al—B, Zr—W, Ti—Zr, Ti—Si, Zn—P, Sn—P, Ti—Zn, Ti—Al, Al—Zr, Sn—Si, Zr—Si, Y—Si, La—Si, Ga—Si, Ti—W, Mo—Si, W—Si, Ti—Sn, Mo—Al, or Zr—P.

Among these, preferred are composite oxides containing, as constituent elements, B—P, B—P—Al, B—P—Ti, B—P—Si, B—P—Zr, Ti—B, Si—Al, Sn—B, Zr—B, Al—P, Ti—P, Fe—P, Al—W, Al—B, Zr—W, Ti—Zr, Ti—Si, Zn—P, or Sn—P because their activity as a catalyst is favorable. Among these, more preferred are composite oxides containing, as constituent elements, B—P, B—P—Al, B—P—Ti, B—P—Si, B—P—Zr, Ti—B, Si-Al, Sn—B, Zr—B, Al—P, Ti—P, or Fe—P, because their production is easy, and most preferred are composite oxides containing, as constituent elements, B—P, B—P—Al, B—P—Ti, B—P—Si, B—P—Zr, or Ti—B, because they are inexpensive and also their production is easy. These composite oxides may contain one or more oxide components other than the main oxide component.

Further, as the solid acid catalyst of the invention, a catalyst which is not uniformly dissolved in the above-described aprotic polar solvent when it is used under the reaction conditions, is preferred. The solid acid catalyst in the invention is not particularly limited by the state when it is packed in or supplied to the reaction system as long as it is in a solid state in the reaction solvent during the reaction. For example, even in the case where the catalyst is provided in a state of a solution in which the catalyst is uniformly dissolved or a uniform liquid, the catalyst only needs to be in a solid state in the reaction solvent during the reaction.

The method for producing the composite oxide serving as the solid acid catalyst is not particularly limited and can be produced by a conventionally known technique. As the method for producing the composite oxide, there are mainly two methods: a method in which the composite oxide is produced from an aqueous solution or an organic solvent solution or a slurry containing a raw material; and a method in which the composite oxide is produced by reacting a raw material at a high temperature. From the viewpoint that a solid acid catalyst having excellent activity is obtained, the former method, particularly, a method in which a solution or a slurry-like liquid containing the respective components is prepared, followed by drying, molding, and calcining, a method in which after a solid containing the respective components is deposited from a solution or a slurry-like liquid containing the respective components, the solid is collected by filtration, centrifugation, or the like, followed by drying, molding, and calcining, or a method in which a solution or a slurry-like liquid containing the respective components is mixed with a molded support, and a solid containing the respective components is supported on the molded support, followed by drying and calcining is preferred. The calcining temperature varies depending on the constituent components of the catalyst, but is selected from a range of generally from 200 to 1000° C., preferably from 300 to 900° C., and the time is selected from a range of generally from 0.5 to 100 hours, preferably from 1 to 30 hours. Further, calcining is most commonly performed in an oxygen-containing gas atmosphere such as air, however, calcining may be performed in an inert gas atmosphere such as nitrogen, argon or helium or in vacuum.

The metal oxide is not particularly limited, however, examples thereof include titanium oxide, niobium oxide, tantalum oxide, tungsten oxide, and molybdenum oxide, and titanium oxide and niobium oxide are preferred from the viewpoint of the catalytic performance. As the method for producing the metal oxide, the same method as the above-described method for producing the composite oxide is used.

The clay compound is not particularly limited, however, either a clay compound produced by hydrothermal synthesis or a naturally produced clay compound can be used. Specific examples thereof include kaolin, mica, and montmorillonite.

The zeolite is not particularly limited, however, either a zeolite produced based on a conventionally known technique such as a hydrothermal synthesis method or a naturally produced zeolite can be used. Specific examples thereof include ZSM-5, mordenite, a beta-type zeolite, and a Y-type zeolite.

Such a clay compound or a zeolite can be used after it is subjected to a pretreatment as appropriate when it is used in the reaction. Specifically, a clay compound or a zeolite undergoing a pretreatment such as a treatment with any of a variety of chemicals such as an acid treatment or an ion exchange treatment, a hot water treatment, or a steam treatment, is preferred.

Among these, as the clay compound, activated clay obtained by treating montmorillonite with an acid is preferred, and as the zeolite, H-USY zeolite obtained by dealuminization of a Y-type zeolite through ion exchange and calcining treatments and H-beta type zeolite are preferred.

Such a clay compound or a zeolite can be used after it is mixed with a binder component such as silica as needed, followed by molding and calcining. The calcining temperature varies depending on the kind or the constituent components of the catalyst, but is generally 200° C. or higher, preferably 300° C. or higher and generally 900° C. or lower, preferably 700° C. or lower. The time is selected from a range of generally 0.5 hours or more, preferably 1 hour or more and generally 100 hours or less, preferably 30 hours or less. Further, calcining is most commonly performed in an oxygen-containing gas atmosphere such as air, however, calcining may be performed in an inert gas atmosphere such as nitrogen, argon or helium or in vacuum.

Examples of the metal sulfate include a hydrate or an anhydride of aluminum sulfate, zirconium sulfate, zinc sulfate, nickel sulfate, ferric sulfate, ferrous sulfate, copper sulfate, magnesium sulfate, chromium sulfate, cobalt sulfate, a rare earth sulfate, and alum or the like. Among these metal sulfates, more preferred are aluminum sulfate, zirconium sulfate, zinc sulfate, nickel sulfate, and ferric sulfate, further more preferred are aluminum sulfate, zirconium sulfate, and zinc sulfate, and most preferred is aluminum sulfate. Such a metal sulfate can be used as it is, but may be used after it is supported on a molded support by impregnating the support with an aqueous solution of the metal sulfate, followed by drying.

Among the above-described solid acid catalysts, the composite oxides and the metal sulfates are preferably used since they are advantageous in terms of reaction yield.

The particle diameter of the solid acid catalyst to be used in the invention is not particularly limited, but is generally 0.0001 mm or more, preferably 0.0005 mm or more, more preferably 0.001 mm or more and generally 50 mm or less, preferably 10 mm or less, more preferably 5 mm or less. If the particle diameter is less than the above-described lower limit, it tends to be difficult to separate the solid acid catalyst, and if the particle diameter exceeds the above-described upper limit, a favorable dispersion state tends not to be obtained.

<Water>

In the method for producing 2-furaldehyde of the invention, although there is no particular limitation, water is preferably used. In the production method of the invention, in order to allow the production reaction of 2-furaldehyde to proceed, it is preferred that water exists in the reaction system. Water plays a role in promoting the swelling or hydration of the raw material and also plays a role in discharging produced 2-furaldehyde to the outside of the reaction system by distillation.

The method for supplying water is not particularly limited and varies depending on the reaction process, however, examples thereof include a method for supplying water in the form of a liquid and a method for supplying water in the form of steam by evaporating water. Alternatively, water may be fed to the reaction system by mixing in advance the sugar raw material containing a hexose as a constituent component, and a necessary amount of water, or by mixing a substance which does not adversely affect the reaction, and water.

<Reaction Conditions>

In the method for producing 2-furaldehyde of the invention, the reaction temperature is not particularly limited, however, in the case where the reaction is performed while discharging 2-furaldehyde which is mainly produced as described later to the outside of the reaction system in a gas phase, the reaction temperature is preferably equal to or higher than the boiling point of 2-furaldehyde and equal to or lower than the boiling point of the solvent. Specifically, the reaction temperature is for example, 140° C. or higher, preferably 160° C. or higher, more preferably 180° C. or higher and generally 300° C. or lower, preferably 280° C. or lower, more preferably 260° C. or lower. If the reaction temperature is lower than the above-described lower limit, the reaction yield may sometimes be insufficient. It is because if the reaction temperature is lower than the above-described lower limit, the reaction rate is low, and if the reaction temperature is lower than the boiling point of 2-furaldehyde, produced 2-furaldehyde stays long in the solvent or in the reaction system, and may sometimes be polymerized or excessively decomposed due to the contact with the solid acid catalyst. If the reaction temperature exceeds the above-described upper limit, there is a possibility that a side reaction of the sugar raw material or an intermediate is prominent, and for example, if the reaction temperature is equal to or higher than the boiling point of the solvent, the solvent may not sufficiently function.

In the method for producing 2-furaldehyde of the invention, the reaction pressure during the reaction is not particularly limited. The reaction pressure can be adjusted to an arbitrary value as long as it is in a range in which the reaction system is maintained in a liquid phase, and produced 2-furaldehyde can be discharged by distillation to the outside of the reaction system along with water.

Further, the reaction to be used in the invention can be performed by allowing a substance which does not adversely affect the reaction such as nitrogen, helium, argon, or carbon dioxide to coexist as appropriate.

<Reaction Process>

The reaction process in the method for producing 2-furaldehyde of the invention can be performed by either a batchwise reaction or a continuous reaction.

In the case of a batchwise reaction, specifically, to a reactor, the sugar raw material containing a hexose as a constituent component, the aprotic polar solvent, and the solid acid catalyst are fed, a reaction is allowed to proceed under heating and stirring, preferably while supplying water, and produced 2-furaldehyde is discharged from the reactor, preferably in a gas phase, more preferably produced 2-furaldehyde can be distilled away from the reactor along with water. In this case, the sugar raw material and the solid acid catalyst are not fed to the reactor at a time, but supplied to the reactor in several batches or a raw material supply method similar to a continuous process by continuously supplying the respective components to the reactor may be adopted.

In the case where a solid sugar raw material is used for the reaction, the shape thereof is not particularly limited, however, preferably, a shape of a small piece with a size of several centimeters or less or a powder shape is suitably used. It is also possible to beforehand perform a treatment of smashing or crushing the raw material inside or outside the reactor before it is subjected to the reaction.

In the invention, in the case where a sugar raw material which is insoluble in the solvent such as cellulose is used, since the solid acid catalyst is also insoluble in the reaction solvent, preferably insoluble in the aprotic polar solvent, solids insoluble in the reaction solvent are present in the reaction system during the reaction. Therefore, the shape and the like of the sugar raw material and the solid acid catalyst are not particularly limited as long as a desired reaction proceeds. Further, the ratio of the amount of the reaction solvent to the amount of the solid components (specifically, the sugar raw material and the solid acid catalyst) in the reaction system is not particularly limited, and an arbitrary ratio can be used. Further, the mixing and stirring method during the production is not particularly limited.

The reaction time in the case of the above-described batchwise reaction varies depending on the kind of the raw material, the using amount of the catalyst, the reaction temperature, the desired yield of 2-furaldehyde to be produced, and so on, and is not particularly limited, but is generally 0.1 hours or more, preferably 0.5 hours or more and generally 50 hours or less, preferably 20 hours or less.

In the case of the continuous reaction, specifically, a method in which the sugar raw material containing a hexose as a constituent component, the aprotic polar solvent, the solid acid catalyst, and preferably water are continuously supplied from one end of a reactor, and the remaining reaction mixture is continuously discharged from the other end of the reactor while discharging produced 2-furaldehyde from the reaction system, preferably discharging produced 2-furaldehyde in a gas phase, more preferably continuously distilling produced 2-furaldehyde away from the reactor along with water can be used. In the continuous reaction, a method in which the catalyst is retained or fixed in the reactor in advance so that the catalyst is not discharged along with the reaction mixture, and the raw material, the aprotic polar solvent, and water are continuously supplied to the reactor can also be adopted.

In the above-described continuous reaction, the retention time in the reactor is not particularly limited, but is generally 0.1 hours or more, preferably 0.5 hours or more and generally 50 hours or less, preferably 20 hours or less.

In the case of the batchwise process in which the sugar raw material containing a hexose as a constituent component, the aprotic polar solvent, and the solid acid catalyst are fed to the reactor, the reaction is allowed to proceed while supplying water under stirring, and produced 2-furaldehyde is discharged from the reaction system, preferably discharged in a gas phase, more preferably distilled away from the reactor along with water, the using amounts of the sugar raw material containing a hexose as a constituent component, the solid acid catalyst, and the aprotic polar solvent are generally such that, with respect to one part by weight of the sugar raw material containing a hexose as a constituent component, the amount of the solid acid catalyst is from 0.001 to 100 parts by weight and the amount of the aprotic polar solvent is from 1 to 1000 parts by weight. In this batchwise process, in the case where the sugar raw material containing a hexose as a constituent component is not fed at a time, but supplied to the reactor in several batches or continuously, generally, the amount of the solid acid catalyst is from 0.001 to 100 parts by weight and the amount of the aprotic polar solvent is from 1 to 1000 parts by weight with respect to one part by weight of the total amount of the raw material to be used in one reaction.

In the case of the continuous process in which the sugar raw material containing a hexose as a constituent component, the aprotic polar solvent, the solid acid catalyst, and water are continuously supplied from one end of the reactor, and the remaining reaction mixture is continuously discharged from the other end of the reactor while discharging produced 2-furaldehyde to the outside of the reaction system, preferably discharging produced 2-furaldehyde in a gas phase, more preferably continuously distilling produced 2-furaldehyde away from the reactor along with water, the using amounts of the sugar raw material containing a hexose as a constituent component, the solid acid catalyst, and the aprotic polar solvent are generally such that, with respect to one part by weight of the sugar raw material containing a hexose as a constituent component, the amount of the solid acid catalyst is from 0.001 to 100 parts by weight and the amount of the aprotic polar solvent is from 1 to 1000 parts by weight. In the continuous process, in the case where the solid acid catalyst is retained or fixed in the reactor in advance so that the catalyst is not discharged along with the reaction mixture, and the sugar raw material containing a hexose as a constituent component, the aprotic polar solvent, and water are continuously supplied to the reactor, generally, with respect to one part by weight of the catalyst in the reactor, the amount of the sugar raw material containing a hexose as a constituent component to be supplied per hour is from 0.01 to 1000 parts by weight and the amount of aprotic polar solvent to be supplied per hour is from 0.01 to 1000000 parts by weight. In the case of the batchwise process, the supply amount of water is generally 0.1 parts by weight or more with respect to one part by weight of the total amount of 2-furaldehyde distilled away from the reactor along with water, and in the case of the continuous process, generally, water is continuously supplied in an amount of 0.1 parts by weight or more per hour with respect to one part by weight of 2-furaldehyde distilled away from the reactor along with water per hour.

The supplying form of the sugar raw material containing a hexose as a constituent component in the continuous reaction is not particularly limited, however, the sugar raw material is preferably supplied in a state of a solution, a paste, or a slurry using water or an aprotic solvent. Further, in the continuous reaction, a method in which at least one member of the solid acid catalyst, the sugar raw material containing a hexose as a constituent component, and the aprotic polar solvent is supplied to the reactor in several batches, a method in which at least one member is supplied stepwise, or a method in which at least one member is supplied to the reactor through another opening or another nozzle is preferably used.

It is also possible to perform a treatment in which the solid acid catalyst, the sugar raw material containing a hexose as a constituent component, and the aprotic polar solvent are uniformly mixed in advance before supplying these members to the reactor.

In the case where produced 2-furaldehyde is discharged to the outside of the reaction system, it is preferred to discharge 2-furaldehyde to the outside of the reaction system so that the amount of 2-furaldehyde is 10% by weight or less with respect to the amount of the solvent in the reaction system in any of the above-described cases.

<Separation and Collection of 2-Furaldehyde>

2-Furaldehyde produced according to the invention can be separated and collected by a common procedure.

In particular, under the preferred reaction conditions of the invention, produced 2-furaldehyde is immediately converted into a gas and removed to the outside of the reaction system, and therefore, labor is not required for separating produced 2-furaldehyde from the solvent or byproducts and the solid acid catalyst remaining in the reaction system. Specifically, 2-furaldehyde is separated and collected by cooling a gas flowing out from the reactor to sequentially condense components starting from a component having a higher boiling point, or once all the liquid components are condensed and collected by cooling, and then water and 2-furaldehyde are separated and collected by distillation. The collected water can be recycled in the reaction system.

The method for purifying 2-furaldehyde produced according to the invention is not particularly limited and the purification can be performed by a conventionally known method. Specifically, a precision distillation method can be exemplified.

The method for storing 2-furaldehyde produced according to the invention is not particularly limited and a conventionally known method can be used, however, for example, a method in which 2-furaldehyde is stored in an airtight container at a temperature near room temperature, a method in which 2-furaldehyde is stored in an inert gas atmosphere, and the like can be exemplified.

In the production method of the invention, in the reaction mixture after the reaction, the unreacted sugar raw material containing a hexose as a constituent component, the aprotic polar solvent, the solid acid catalyst, insoluble byproducts, soluble byproducts, etc. are contained. The solid acid catalyst used in the invention can be easily collected by a method such as filtration or centrifugation along with the other insoluble components. The separation of the solid acid catalyst from the other insoluble components can be performed by utilizing a difference in density or a difference in particle diameter. In the case where the solid acid catalyst dissolves in a specific solvent, the solid acid catalyst can be collected by dissolving the solid acid catalyst in the solvent, followed by separation from the insoluble components. Further, it is also possible to collect the solid acid catalyst after burning the insoluble components. By doing this, the separated and collected solid acid catalyst can be recycled in the reaction system.

Further, from the reaction mixture after the reaction, the aprotic polar solvent separated from the catalyst and the other insoluble components by filtration or centrifugation may be recycled in the reaction system after removing soluble byproducts by distillation or the like as needed.

<2-Furaldehyde>

2-Furaldehyde obtained according to the invention can be used as a solvent. Further, according to a conventionally known method, it can be used in the application as a raw material for producing furan, tetrahydrofuran, a furan resin, etc.

Specifically, by subjecting 2-furaldehyde to a hydrogenation reaction in the presence of a catalyst, furfuryl alcohol which is a raw material for producing a furan resin can be obtained. Further, by subjecting 2-furaldehyde to a decarbonylation reaction in the presence of a catalyst, furan can be obtained. By subjecting the thus obtained furan to a hydrogenation reaction in the presence of a catalyst, furan can be converted into tetrahydrofuran.

EXAMPLES

Hereinafter, the invention will be more specifically described with reference to Examples, however, the invention is not limited to these Examples as long as it does not exceed the gist of the invention.

Example 1

<Solid Acid Catalyst: Preparation of B—P—Al Composite Oxide>

5.33 g of boric acid (86.2 mmol, manufactured by Kishida Chemical Co., Ltd., special grade), 9.94 g of 85% phosphoric acid (86.2 mmol in terms of phosphoric acid, manufactured by Junsei Chemical Co., Ltd., special grade), and 6.47 g of aluminum nitrate nonahydrate (17.2 mmol, manufactured by Kishida Chemical Co., Ltd., special grade) were dissolved in 100 ml of desalted water. The resulting solution was stirred for 1 hour, followed by evaporation to dryness on an evaporating dish. The obtained solid was calcined at 400° C. for 2 hours in an air stream, whereby a B—P—Al composite oxide was obtained (feed composition (molar ratio): B/P/Al=1.0/1.0/0.2).

<Production of 2-Furaldehyde from Cellulose Using B—P—Al Composite Oxide as Solid Acid Catalyst>

To a 100-ml four-necked flask in which a Teflon (registered trademark) stirring bar was placed, a Teflon (registered trademark)-coated thermocouple (for measuring the temperature of the reaction mixture), a Claisen connecting tube and a Liebig condenser (for cooling a distillate liquid), a 50-ml Erlenmeyer flask (a distillate liquid receiver) were fitted. A tape heater was wound around the portion of the Claisen connecting tube, and the tape heater was covered with a heat insulating material made of silicone rubber. Nitrogen was allowed to flow through the reactor at 20 ml/min so that the atmosphere in the reactor was brought into a nitrogen atmosphere. Thereafter, 50.0 g of sulfolane (manufactured by Kishida Chemical Co., Ltd., special grade) as the aprotic polar solvent and 2.0 g of the above B—P—Al composite oxide as the solid acid catalyst were added thereto and mixed by stirring. The temperature of an oil bath was raised to 230° C. over 40 minutes using a program temperature controller and maintained as such. The heating of the tape heater (the temperature of the outer surface of the Claisen connecting tube was set to 120° C.) was initiated simultaneously with the initiation of raising of the temperature of the oil bath. When the temperature of the oil bath reached 230° C., a slurry (containing cellulose at 25% by weight) prepared by mixing cellulose (manufactured by Aldrich Co., Ltd., Cellulose, microcrystalline, powder, up to 20 μm) and desalted water was supplied at a rate of 8.0 g/hour from one end of the four-necked flask.

The reaction initiation time was defined as the time when the supply of the slurry was initiated, and when the reaction time was 0.5 hours, the Erlenmeyer flask serving as the distillate liquid receiver was replaced with a sampling receiver (containing 30 ml of tetrahydrofuran (manufactured by Junsei Chemical Co., Ltd., special grade) as a solvent for trapping the distillate and 0.5 ml of diethylene glycol diethyl ether (manufactured by Kishida Chemical Co., Ltd., special grade) as an internal standard material for gas chromatography analysis). Thereafter, the sampling receiver was replaced hourly (0.5-1.5 hours, 1.5-2.5 hours, 2.5-3.5 hours, 3.5-4.5 hours, and 4.5-5.5 hours) to collect the receiver containing the distillate liquid. The collected receiver was shaken to stir the contents well, and the production amount of 2-furaldehyde (hereinafter FAL is used as the abbreviation) was determined by gas chromatography analysis (an internal standard method).

In the analysis of 2-furaldehyde, a gas chromatograph GC-2014 (FID) manufactured by Shimadzu Corporation was used. For the waveform processing, Chromatopac C-R8A manufactured by Shimadzu Corporation was used.

GC Analysis Conditions

Column: FON 10%/Celite 545A 80/100, 3 m (stainless steel)

Carrier gas: nitrogen (30 ml/min)

Column temperature: 140° C. (15 min)→raised to 240° C. (20° C./min)→240° C. (25 min)

INJ: 200° C.

DET: 240° C.

The yield of 2-furaldehyde (FAL) was determined according to the following formula.

[FAL yield (mol %)]=[mole number of produced FAL (analytical value of gas chromatography)]/ [mole number of hexose units supplied per hour]×100.

Incidentally, the mole number of hexose units was calculated by assuming that cellulose is a polymer composed of 100% hexose (($C_6H_{10}O_5)_n$, formula weight: (162.14)n). The results are shown in Table 1.

Example 2

A procedure was performed in the same manner as in Example 1 except that 2.0 g of aluminum sulfate 14-18 hydrate (manufactured by Kishida Chemical Co., Ltd., special grade) was used as the solid acid catalyst. The results are shown in Table 1.

Comparative Example 1

2-Furaldehyde was produced in the same manner as in Example 1 except that 0.5 mmol of sulfuric acid (manufactured by Kishida Chemical Co., Ltd., 98%, special grade) was used in place of the B—P—Al composite oxide serving as the solid acid catalyst. The results are shown in Table 1.

In the case where sulfuric acid which is uniformly dissolved in the aprotic polar solvent was used as the catalyst, the yield of 2-furaldehyde drastically decreased as the reaction time increased.

Comparative Example 2

A procedure was performed in the same manner as in Comparative Example 1 except that 2.0 mmol of sulfuric acid (manufactured by Kishida Chemical Co., Ltd., 98%, special grade) was used as the catalyst. The results are shown in Table 1.

Even if the using amount of sulfuric acid was increased from 0.5 mmol in Comparative Example 1 to 2.0 mmol, an improvement effect on the yield of 2-furaldehyde was low, and also a decrease in yield over time could not be suppressed.

TABLE 1

|  | Catalyst | Reaction time | FAL yield (mol %) | Temperature of reaction mixture | FAL yield (mol %) (average in 0.5-5.5 h) |
|---|---|---|---|---|---|
| Example 1 | B—P—Al composite oxide | 0.5 h-1.5 h<br>1.5 h-2.5 h | 21.1<br>30.7 | 222° C.<br>223° C. | 29.5 |

TABLE 1-continued

|  | Catalyst | Reaction time | FAL yield (mol %) | Temperature of reaction mixture | FAL yield (mol %) (average in 0.5-5.5 h) |
|---|---|---|---|---|---|
|  | 2.0 g | 2.5 h-3.5 h | 32.4 | 223° C. |  |
|  |  | 3.5 h-4.5 h | 33.1 | 223° C. |  |
|  |  | 4.5 h-5.5 h | 30.1 | 221° C. |  |
| Example 2 | Aluminum sulfate | 0.5 h-1.5 h | 14.4 | 223° C. | 28.1 |
|  | 14-18 hydrate | 1.5 h-2.5 h | 27.2 | 224° C. |  |
|  | 2.0 g | 2.5 h-3.5 h | 32.7 | 224° C. |  |
|  |  | 3.5 h-4.5 h | 32.3 | 223° C. |  |
|  |  | 4.5 h-5.5 h | 33.7 | 223° C. |  |
| Comparative Example 1 | Sulfuric acid 0.5 mmol | 0.5 h-1.5 h | 6.5 | 223° C. | 2.8 |
|  |  | 1.5 h-2.5 h | 2.6 | 223° C. |  |
|  |  | 2.5 h-3.5 h | 1.8 | 223° C. |  |
|  |  | 3.5 h-4.5 h | 1.6 | 223° C. |  |
|  |  | 4.5 h-5.5 h | 1.5 | 223° C. |  |
| Comparative Example 2 | Sulfuric acid 2.0 mmol | 0.5 h-1.5 h | 9.2 | 223° C. | 3.0 |
|  |  | 1.5 h-2.5 h | 2.2 | 224° C. |  |
|  |  | 2.5 h-3.5 h | 1.3 | 224° C. |  |
|  |  | 3.5 h-4.5 h | 1.1 | 223° C. |  |
|  |  | 4.5 h-5.5 h | 1.1 | 223° C. |  |

Example 3

2-Furaldehyde was produced in the same manner as in Example 1 except that 2.0 g of a B—P composite oxide was used as the solid acid catalyst. An average of the hourly yields of 2-furaldehyde in the reaction time between 0.5 and 5.5 hours is shown in Table 2.

The B—P composite oxide was prepared by the following method.

10.13 g of boric acid (163.8 mmol, manufactured by Kishida Chemical Co., Ltd., special grade), 15.11 g of 85% phosphoric acid (131.0 mmol in terms of phosphoric acid, manufactured by Junsei Chemical Co., Ltd., special grade), and 125 ml of desalted water were mixed and dissolved by heating. The resulting solution was evaporated to dryness on an evaporating dish, and the obtained solid was calcined at 400° C. for 2 hours in an air stream, whereby the B—P composite oxide was obtained (feed composition (molar ratio): B/P=1.0/0.8).

Example 4

A procedure was performed in the same manner as in Example 1 except that 2.0 g of a Ti—B composite oxide was used as the solid acid catalyst. An average of the hourly yields of 2-furaldehyde in the reaction time between 0.5 and 5.5 hours is shown in Table 2.

The Ti—B composite oxide was prepared by the following method.

70.51 g of an aqueous solution of titanium sulfate (manufactured by Kishida Chemical Co., Ltd., containing $Ti(SO_4)_2$ at 40% by weight and $H_2SO_4$ at 30% by weight, 117.5 mmol in terms of Ti) was mixed with 200 ml of desalted water to form a uniform solution. While vigorously stirring the resulting solution, a mixed solution of 82.2 g of a 28% aqueous ammonia solution (manufactured by Kishida Chemical Co., Ltd., special grade) and 165 ml of desalted water was added dropwise thereto over 0.5 hours, and the resulting mixture was stirred as such for 2 hours. Then, the mixture was left to stand overnight for aging. After the obtained precipitate was filtered, suspension washing of the residue using 300 ml of desalted water was repeated 4 times. The obtained solid was added to a solution obtained by dissolving 1.09 g of boric acid (17.6 mmol, manufactured by Kishida Chemical Co., Ltd., special grade) in 100 ml of desalted water, and the resulting mixture was stirred at room temperature for 1 hour. Thereafter, the mixture was evaporated to dryness on an evaporating dish, followed by drying at 120° C. The solid obtained by drying was calcined at 550° C. for 2 hours in an air stream, whereby the Ti—B composite oxide was obtained (feed composition (molar ratio): Ti/B=1.0/0.15).

Example 5

A procedure was performed in the same manner as in Example 1 except that 2.0 g of a Ti—B—P composite oxide was used as the solid acid catalyst. An average of the hourly yields of 2-furaldehyde in the reaction time between 0.5 and 5.5 hours is shown in Table 2.

The Ti—B—P composite oxide was prepared by the following method.

2.33 g of boric acid (37.7 mmol, manufactured by Kishida Chemical Co., Ltd., special grade) and 4.34 g of 85% phosphoric acid (37.7 mmol in terms of phosphoric acid, manufactured by Junsei Chemical Co., Ltd., special grade) were dissolved in 100 ml of desalted water. While stirring the resulting solution, 6.02 g of titania (JRC-TIO-4, 75.3 mmol in terms of Ti, a reference catalyst of Catalysis Society of Japan) was added thereto, and the resulting mixture was stirred as such for 1 hour, followed by evaporation to dryness on an evaporating dish. The obtained solid was calcined at 400° C. for 2 hours in an air stream, whereby the Ti—B—P composite oxide was obtained (feed composition (molar ratio): Ti/B/P=1.0/0.5/0.5).

Example 6

A procedure was performed in the same manner as in Example 1 except that 2.0 g of a B—P—Si composite oxide was used as the solid acid catalyst. An average of the hourly yields of 2-furaldehyde in the reaction time between 0.5 and 5.5 hours is shown in Table 2.

The B—P—Si composite oxide was prepared by the following method.

To a 100-ml four-necked flask equipped with a stirring blade, 2.03 g of boric acid (32.8 mmol, manufactured by Kishida Chemical Co., Ltd., special grade), 3.02 g of 85% phosphoric acid (26.2 mmol in terms of phosphoric acid, manufactured by Junsei Chemical Co., Ltd., special grade), and 15 ml of desalted water were fed and dissolved by stirring in an oil bath at 80° C. to form a uniform solution. Thereafter, 7.00 g of silica (manufactured by Fuji Silysia Co., Ltd., CARiACT Q-15, 70-500 jam, 116.5 mmol in terms of Si) was added thereto, and the resulting mixture was gently stirred for 1 hour. After the mixture was dried for 2 hours in an oil bath at 80° C. while passing dry nitrogen through the flask, the temperature of the oil bath was raised from 80° C. to 120° C. over 2 hours, and the content in the flask was dried at 120° C. for 1 hour. The obtained solid was calcined at 400° C. for 2 hours in an air stream, whereby the B—P—Si composite oxide was obtained (feed composition (molar ratio): B/P/Si=1.0/0.8/3.6).

Example 7

A procedure was performed in the same manner as in Example 1 except that 2.0 g of a Zr—B—P composite oxide was used as the solid acid catalyst. An average of the hourly yields of 2-furaldehyde in the reaction time between 0.5 and 5.5 hours is shown in Table 2.

The Zr—B—P composite oxide was prepared by the following method.

1.76 g of boric acid (28.4 mmol, manufactured by Kishida Chemical Co., Ltd., special grade) and 3.27 g of 85% phosphoric acid (28.4 mmol in terms of phosphoric acid, manufactured by Junsei Chemical Co., Ltd., special grade) were dissolved in 100 ml of desalted water. While stirring the resulting solution, 8.85 g of zirconium hydroxide (contained at 79.1% by weight in terms of $ZrO_2$, 56.8 mmol in terms of Zr, manufactured by Mitsuwa Chemical Co., Ltd.) was added thereto, and the resulting mixture was stirred as such for 1 hour, followed by evaporation to dryness on an evaporating dish. The obtained solid was calcined at 400° C. for 2 hours in an air stream, whereby the Zr—B—P composite oxide was obtained (feed composition (molar ratio): Zr/B/P=1.0/0.5/0.5).

Example 8

A procedure was performed in the same manner as in Example 1 except that 2.0 g of silica-alumina (manufactured by Nikki Kagaku Co., Ltd., N633-HN ($SiO_2$ at 66.5% by weight and $Al_2O_3$ at 25.1% by weight)) was used as the solid acid catalyst. An average of the hourly yields of 2-furaldehyde in the reaction time between 0.5 and 5.5 hours is shown in Table 2.

Example 9

A procedure was performed in the same manner as in Example 1 except that 2.0 g of zirconium sulfate tetrahydrate (manufactured by Kishida Chemical Co., Ltd., for chemical purposes) was used as the solid acid catalyst. An average of the hourly yields of 2-furaldehyde in the reaction time between 0.5 and 5.5 hours is shown in Table 2.

Example 10

A procedure was performed in the same manner as in Example 1 except that 2.0 g of H-USY zeolite (manufactured by Tosoh Co., Ltd., HSZ-330HUA (Si/2Al=6, Lot. C2-0719)) was used as the solid acid catalyst. An average of the hourly yields of 2-furaldehyde in the reaction time between 0.5 and 5.5 hours is shown in Table 2.

Example 11

A procedure was performed in the same manner as in Example 1 except that 2.0 g of a Sn—B composite oxide was used as the solid acid catalyst. An average of the hourly yields of 2-furaldehyde in the reaction time between 0.5 and 5.5 hours is shown in Table 2.

The Sn—B composite oxide was prepared by the following method.

0.969 g of boric acid (15.7 mmol, manufactured by Kishida Chemical Co., Ltd., special grade) was dissolved in 100 ml of desalted water. While stirring the resulting solution, 10.58 g of stannic acid (62.7 mmol, manufactured by Kojundo Chemical Laboratory. Co., Ltd.) was added thereto, and the resulting mixture was stirred as such for 1 hour, followed by evaporation to dryness on an evaporating dish. The obtained solid was calcined at 400° C. for 2 hours in an air stream, whereby the Sn—B composite oxide was obtained (feed composition (molar ratio): Sn/B=1.0/0.25).

Example 12

A procedure was performed in the same manner as in Example 1 except that 2.0 g of an Al—P composite oxide was used as the solid acid catalyst. An average of the hourly yields of 2-furaldehyde in the reaction time between 0.5 and 5.5 hours is shown in Table 2.

The Al—P composite oxide was prepared by the following method.

30.76 g of aluminum nitrate nonahydrate (82.0 mmol, manufactured by Kishida Chemical Co., Ltd., special grade) and 9.45 g of 85% phosphoric acid (82.0 mmol in terms of phosphoric acid, manufactured by Junsei Chemical Co., Ltd., special grade) were dissolved in 250 ml of desalted water. While stirring the resulting solution, a mixed solution of 18.0 g of a 28% aqueous ammonia solution (manufactured by Kishida Chemical Co., Ltd., special grade) and 36 ml of desalted water was added dropwise thereto over about 15 minutes, and the resulting mixture was stirred as such for 2 hours. Then, the mixture was left to stand overnight for aging. The formed precipitate was collected by filtration, and then stirred for 1 hour using 300 ml of desalted water, followed by filtration, whereby a solid was obtained. The obtained solid was dried at 120° C., and then calcined at 550° C. for 2 hours in an air stream, whereby the Al—P composite oxide was obtained (feed composition (molar ratio): Al/P=1.0/1.0).

Example 13

A procedure was performed in the same manner as in Example 1 except that 2.0 g of zinc sulfate heptahydrate (manufactured by Kishida Chemical Co., Ltd., special grade) was used as the solid acid catalyst. An average of the hourly yields of 2-furaldehyde in the reaction time between 0.5 and 5.5 hours is shown in Table 2.

Example 14

A procedure was performed in the same manner as in Example 1 except that 2.0 g of activated clay (manufactured by Sigma-Aldrich Co., Ltd., montmorillonite K10) was used as the solid acid catalyst. An average of the hourly yields of 2-furaldehyde in the reaction time between 0.5 and 5.5 hours is shown in Table 2.

Example 15

A procedure was performed in the same manner as in Example 1 except that 2.0 g of a Ti—P composite oxide was used as the solid acid catalyst. An average of the hourly yields of 2-furaldehyde in the reaction time between 0.5 and 5.5 hours is shown in Table 2.

The Ti—P composite oxide was prepared by the following method.

34.38 g of an aqueous solution of titanium sulfate (manufactured by Kishida Chemical Co., Ltd., containing $Ti(SO_4)_2$ at 40% by weight and $H_2SO_4$ at 30% by weight, 57.3 mmol in terms of Ti) was mixed with 200 ml of desalted water to form a uniform solution. While vigorously stirring the resulting solution, a mixed solution of 40.1 g of a 28% aqueous ammonia solution (manufactured by Kishida Chemical Co., Ltd., special grade) and 80 ml of desalted water was added dropwise thereto over 0.5 hours, and the resulting mixture was stirred as such for 2 hours. Then, the mixture was left to stand overnight for aging. After filtration of the precipitate and suspension washing using 300 ml of desalted water were repeated 4 times, the obtained solid was added to a solution obtained by dissolving 8.81 g of 85% phosphoric acid (76.4 mmol in terms of phosphoric acid, manufactured by Junsei Chemical Co., Ltd., special grade) in 100 ml of desalted water, and the resulting mixture was stirred at room temperature for 1 hour. Thereafter, the mixture was evaporated to dryness on an evaporating dish, followed by drying at 120° C. The solid obtained by drying was calcined at 550° C. for 2 hours in an air stream, whereby the Ti—P composite oxide was obtained (feed composition (molar ratio): Ti/P=1.0/1.33).

Example 16

A procedure was performed in the same manner as in Example 1 except that 2.0 g of a Zr—B composite oxide was used as the solid acid catalyst. An average of the hourly yields of 2-furaldehyde in the reaction time between 0.5 and 5.5 hours is shown in Table 2.

The Zr—B composite oxide was prepared by the following method.

20.26 g of zirconium oxynitrate dihydrate (75.8 mmol, manufactured by Kishida Chemical Co., Ltd., special grade) was dissolved in 250 ml of desalted water. While stirring the resulting solution, a mixed solution of 11.06 g of a 28% aqueous ammonia solution (manufactured by Kishida Chemical Co., Ltd., special grade) and 22 ml of desalted water was added dropwise thereto over about 30 minutes, and the resulting mixture was stirred as such for 2 hours. Then, the mixture was left to stand overnight for aging. The formed precipitate was collected by filtration, and then stirred for 1 hour using 300 ml of desalted water, followed by filtration, whereby a solid was obtained. The obtained solid was added to a solution obtained by dissolving 1.172 g of boric acid (18.95 mmol, manufactured by Kishida Chemical Co., Ltd., special grade) in 100 ml of desalted water, and the resulting mixture was stirred at room temperature for 1 hour. Thereafter, the mixture was evaporated to dryness on an evaporating dish, and the obtained solid was calcined at 550° C. for 2 hours in an air stream, whereby the Zr—B composite oxide was obtained (feed composition (molar ratio): Zr/B=1.0/0.25).

Example 17

A procedure was performed in the same manner as in Example 1 except that 2.0 g of H-beta type zeolite (prepared by calcination of HSZ-930NHA (manufactured by Tosoh Co., Ltd., Si/2Al=27, Lot. 93NA8802) at 550° C. for 10 hours in an air stream) was used as the solid acid catalyst. An average of the hourly yields of 2-furaldehyde in the reaction time between 0.5 and 5.5 hours is shown in Table 2.

Example 18

A procedure was performed in the same manner as in Example 1 except that 2.0 g of a Fe—P composite oxide was used as the solid acid catalyst. An average of the hourly yields of 2-furaldehyde in the reaction time between 0.5 and 5.5 hours is shown in Table 2.

The Fe—P composite oxide was prepared by the following method.

26.79 g of ferric nitrate nonahydrate (66.3 mmol, manufactured by Kishida Chemical Co., Ltd., special grade) and 7.64 g of 85% phosphoric acid (66.3 mmol in terms of phosphoric acid, manufactured by Junsei Chemical Co., Ltd., special grade) were dissolved in 250 ml of desalted water. While stirring the resulting solution, a mixed solution of 14.5 g of a 28% aqueous ammonia solution (manufactured by Kishida Chemical Co., Ltd., special grade) and 29 ml of desalted water was added dropwise thereto over about 15 minutes, and the resulting mixture was stirred as such for 2 hours. Then, the mixture was left to stand overnight for aging. The formed precipitate was collected by filtration, and then suspension washing using 300 ml of desalted water was performed. Thereafter, the obtained solid was dried at 120° C., and then calcined at 550° C. for 2 hours in an air stream, whereby the Fe—P composite oxide was obtained (feed composition (molar ratio): Fe/P=1.0/1.0).

Example 19

A procedure was performed in the same manner as in Example 1 except that 2.0 g of an Al—W composite oxide was used as the solid acid catalyst. An average of the hourly yields of 2-furaldehyde in the reaction time between 0.5 and 5.5 hours is shown in Table 2.

The Al—W composite oxide was prepared by the following method.

38.53 g of aluminum nitrate nonahydrate (102.7 mmol, manufactured by Kishida Chemical Co., Ltd., special grade) was dissolved in 250 ml of desalted water. While stirring the resulting solution, a mixed solution of 22.5 g of a 28% aqueous ammonia solution (manufactured by Kishida Chemical Co., Ltd., special grade) and 45 ml of desalted water was added dropwise thereto over about 15 minutes, and the resulting mixture was stirred as such for 2 hours. Then, the mixture was left to stand overnight for aging. The formed precipitate was collected by filtration, and stirred for 1 hour using 300 ml of desalted water, followed by filtration, whereby a solid was obtained. The obtained solid was added to a solution obtained by dissolving 5.36 g of ammonium paratungstate pentahydrate (20.5 mmol in terms of W, manufactured by Kishida Chemical Co., Ltd., first class grade) in 180 ml of desalted water, and the resulting mixture was stirred at room temperature for 1 hour. Thereafter, the mixture was evaporated to dryness, followed by drying at 120° C. The solid obtained by drying was calcined at 550° C. for 2 hours in an air stream, whereby the Al—W composite oxide was obtained (feed composition (molar ratio): Al/W=1.0/0.2).

Example 20

A procedure was performed in the same manner as in Example 1 except that 2.0 g of ferric sulfate n-hydrate (manufactured by Kishida Chemical Co., Ltd., special grade) was used as the solid acid catalyst. An average of the hourly yields of 2-furaldehyde in the reaction time between 0.5 and 5.5 hours is shown in Table 2.

Example 21

A procedure was performed in the same manner as in Example 1 except that 2.0 g of an Al—B composite oxide was used as the solid acid catalyst. An average of the hourly yields of 2-furaldehyde in the reaction time between 0.5 and 5.5 hours is shown in Table 2.

The Al—B composite oxide was prepared by the following method.

66.74 g of aluminum nitrate nonahydrate (177.9 mmol, manufactured by Kishida Chemical Co., Ltd., special grade) was dissolved in 250 ml of desalted water. While stirring the resulting solution, a mixed solution of 39.0 g of a 28% aqueous ammonia solution (manufactured by Kishida Chemical Co., Ltd., special grade) and 78 ml of desalted water was added dropwise thereto over about 15 minutes, and the resulting mixture was stirred as such for 2 hours. Then, the mixture was left to stand overnight for aging. The formed precipitate was collected by filtration, and stirred for 1 hour using 300 ml of desalted water, followed by filtration, whereby a solid was obtained. The obtained solid was added to a solution obtained by dissolving 1.65 g of boric acid (26.7 mmol, manufactured by Kishida Chemical Co., Ltd., special grade) in 200 ml of desalted water, and the resulting mixture was stirred at room temperature for 1 hour. Thereafter, the mixture was evaporated to dryness, followed by drying at 120° C. The solid obtained by drying was calcined at 550° C. for 2 hours in an air stream, whereby the Al—B composite oxide was obtained (feed composition (molar ratio): Al/B=1.0/0.15).

Example 22

A procedure was performed in the same manner as in Example 1 except that 2.0 g of a Zr—W composite oxide was used as the solid acid catalyst. An average of the hourly yields of 2-furaldehyde in the reaction time between 0.5 and 5.5 hours is shown in Table 2.

The Zr—W composite oxide was prepared by the following method.

18.25 g of zirconium oxynitrate dihydrate (68.3 mmol, manufactured by Kishida Chemical Co., Ltd., special grade) was dissolved in 250 ml of desalted water. While stirring the resulting solution, a mixed solution of 10.0 g of a 28% aqueous ammonia solution (manufactured by Kishida Chemical Co., Ltd., special grade) and 20 ml of desalted water was added dropwise thereto over about 15 minutes, and the resulting mixture was stirred as such for 2 hours. Then, the mixture was left to stand overnight for aging. The formed precipitate was collected by filtration, and then stirred for 1 hour using 300 ml of desalted water, followed by filtration, whereby a solid was obtained. The obtained solid was added to a solution obtained by dissolving 1.78 g of ammonium paratungstate pentahydrate (6.83 mmol in terms of W, manufactured by Kishida Chemical Co., Ltd., first class grade) in 100 ml of desalted water, and the resulting mixture was stirred at room temperature for 1 hour. Thereafter, the mixture was evaporated to dryness, followed by drying at 120° C. The solid obtained by drying was calcined at 550° C. for 2 hours in an air stream, whereby the Zr—W composite oxide was obtained (feed composition (molar ratio): Zr/W=1.0/0.1).

Example 23

A procedure was performed in the same manner as in Example 1 except that 2.0 g of a Ti—Zr composite oxide was used as the solid acid catalyst. An average of the hourly yields of 2-furaldehyde in the reaction time between 0.5 and 5.5 hours is shown in Table 2.

The Ti—Zr composite oxide was prepared by the following method.

42.4 g of an aqueous solution of titanium sulfate (manufactured by Kishida Chemical Co., Ltd., containing $Ti(SO_4)_2$ at 40% by weight and $H_2SO_4$ at 30% by weight, 70.7 mmol in terms of Ti) and 12.6 g of zirconium sulfate tetrahydrate (35.3 mmol, manufactured by Kishida Chemical Co., Ltd., special grade) were mixed with 200 ml of desalted water to form a uniform solution. While vigorously stirring the resulting solution, a mixed solution of 52.0 g of a 28% aqueous ammonia solution (manufactured by Kishida Chemical Co., Ltd., special grade) and 104 ml of desalted water was added dropwise thereto over 0.5 hours, and the resulting mixture was stirred as such for 2 hours. Then, the mixture was left to stand overnight for aging. After filtration of the precipitate and suspension washing using 300 ml of desalted water were repeated 3 times, the obtained solid was dried at 120° C., followed by calcining at 550° C. for 2 hours in an air stream, whereby the Ti—Zr composite oxide was obtained (feed composition (molar ratio): Ti/Zr=1.0/0.5).

Example 24

A procedure was performed in the same manner as in Example 1 except that 2.0 g of a Ti—Si composite oxide was used as the solid acid catalyst. An average of the hourly yields of 2-furaldehyde in the reaction time between 0.5 and 5.5 hours is shown in Table 2.

The Ti—Si composite oxide was prepared by the following method.

65.28 g of an aqueous solution of titanium sulfate (manufactured by Kishida Chemical Co., Ltd., containing $Ti(SO_4)_2$ at 40% by weight and $H_2SO_4$ at 30% by weight, 108.8 mmol in terms of Ti) was dissolved in 200 ml of desalted water. While stirring the resulting solution, 40 ml of ethanol (manufactured by Junsei Chemical Co., Ltd., special grade), 4.53 g of ethyl silicate (21.8 mmol, manufactured by Kishida Chemical Co., Ltd., special grade), and 150.4 g of urea (manufactured by Kishida Chemical Co., Ltd., special grade) were added thereto. The resulting mixture was heat-treated at 85° C. for 8 hours to form a precipitate. Then, the mixture was left to stand overnight for aging. The formed precipitate was collected by filtration, and suspension washing using 300 ml of desalted water was repeated 3 times. Then, the obtained solid was dried at 120° C., followed by calcining at 550° C. for 2 hours in an air stream, whereby the Ti—Si composite oxide was obtained (feed composition (molar ratio): Ti/Si=1.0/0.2).

Example 25

A procedure was performed in the same manner as in Example 1 except that 2.0 g of a Zn—P composite oxide was used as the solid acid catalyst. An average of the hourly yields of 2-furaldehyde in the reaction time between 0.5 and 5.5 hours is shown in Table 2.

The Zn—P composite oxide was prepared by the following method.

19.52 g of zinc nitrate hexahydrate (65.6 mmol, manufactured by Kishida Chemical Co., Ltd., special grade) and 7.57 g of 85% phosphoric acid (65.6 mmol in terms of phosphoric acid, manufactured by Junsei Chemical Co., Ltd., special grade) were dissolved in 250 ml of desalted water. While stirring the resulting solution, a mixed solution of 7.98 g of a 28% aqueous ammonia solution (manufactured by Kishida Chemical Co., Ltd., special grade) and 16 ml of desalted water was added dropwise thereto over about 15 minutes, and the resulting mixture was stirred as such for 2 hours. Then, the mixture was left to stand overnight for aging. The formed precipitate was collected by filtration, and then stirred for 1 hour using 300 ml of desalted water, followed by filtration, whereby a solid was obtained. Thereafter, the obtained solid was dried at 120° C., and then calcined at 550° C. for 2 hours in an air stream, whereby the Zn—P composite oxide was obtained (feed composition (molar ratio): Zn/P=1.0/1.0).

Example 26

A procedure was performed in the same manner as in Example 1 except that 2.0 g of nickel sulfate hexahydrate (manufactured by Kishida Chemical Co., Ltd., special grade) was used as the solid acid catalyst. An average of the hourly yields of 2-furaldehyde in the reaction time between 0.5 and 5.5 hours is shown in Table 2.

Example 27

A procedure was performed in the same manner as in Example 1 except that 2.0 g of a Sn—P composite oxide was used as the solid acid catalyst. An average of the hourly yields of 2-furaldehyde in the reaction time between 0.5 and 5.5 hours is shown in Table 2.

The Sn—P composite oxide was prepared by the following method.

14.29 g of stannic chloride pentahydrate (40.8 mmol, manufactured by Sigma-Aldrich Co., Ltd.) was dissolved in 136 ml of desalted water. While stirring the resulting solution, a mixed solution of 6.27 g of 85% phosphoric acid (54.4 mmol in terms of phosphoric acid, manufactured by Junsei Chemical Co., Ltd., special grade) and 90 ml of desalted water was added dropwise thereto over about 15 minutes, and the resulting mixture was stirred as such at room temperature for 1 hour. While stirring the resulting slurry, a mixed solution of 10.4 g of a 28% aqueous ammonia solution (manufactured by Kishida Chemical Co., Ltd., special grade) and 21 ml of desalted water was added dropwise thereto over about 15 minutes, and the resulting mixture was stirred as such for 2 hours. Then, the mixture was left to stand overnight for aging. The formed precipitate was collected by filtration, and suspension washing using 300 ml of desalted water was repeated 3 times. Then, the obtained solid was dried at 120° C., followed by calcining at 550° C. for 2 hours in an air stream, whereby the Sn—P composite oxide was obtained (feed composition (molar ratio): Sn/P=1.0/1.33).

TABLE 2

| Catalyst | | FAL yield (mol %) (average in 0.5-5.5 h) | Temperature of reaction mixture (average in 0.5-5.5 h) |
| --- | --- | --- | --- |
| Example 3 | B—P composite oxide | 28.7 | 223° C. |
| Example 4 | Ti—B composite oxide | 25.8 | 223° C. |
| Example 5 | Ti—B—P composite oxide | 24.6 | 223° C. |

TABLE 2-continued

| Catalyst | | FAL yield (mol %) (average in 0.5-5.5 h) | Temperature of reaction mixture (average in 0.5-5.5 h) |
| --- | --- | --- | --- |
| Example 6 | B—P—Si composite oxide | 24.0 | 224° C. |
| Example 7 | Zr—B—P composite oxide | 21.8 | 223° C. |
| Example 8 | Silica-alumina | 17.1 | 223° C. |
| Example 9 | Zirconium sulfate tetrahydrate | 17.1 | 224° C. |
| Example 10 | H-USY zeolite | 16.7 | 223° C. |
| Example 11 | Sn—B composite oxide | 13.6 | 223° C. |
| Example 12 | Al—P composite oxide | 13.2 | 224° C. |
| Example 13 | Zinc sulfate heptahydrate | 12.9 | 224° C. |
| Example 14 | Activated clay | 11.4 | 223° C. |
| Example 15 | Ti—P composite oxide | 11.4 | 223° C. |
| Example 16 | Zr—B composite oxide | 11.2 | 223° C. |
| Example 17 | H-beta type composite oxide | 10.8 | 223° C. |
| Example 18 | Fe—P composite oxide | 10.4 | 223° C. |
| Example 19 | Al—W composite oxide | 8.6 | 224° C. |
| Example 20 | Ferric sulfate n-hydrate | 8.1 | 224° C. |
| Example 21 | Al—B composite oxide | 7.8 | 224° C. |
| Example 22 | Zr—W composite oxide | 7.5 | 223° C. |
| Example 23 | Ti—Zr composite oxide | 7.5 | 224° C. |
| Example 24 | Ti—Si composite oxide | 6.2 | 224° C. |
| Example 25 | Zn—P composite oxide | 4.8 | 223° C. |
| Example 26 | Nickel sulfate hexahydrate | 4.8 | 224° C. |
| Example 27 | Sn—P composite oxide | 4.1 | 224° C. |

Example 28

A procedure was performed in the same manner as in Example 2 except that 50.0 g of phthalide (manufactured by Tokyo Chemical Industry Co., Ltd.) was used as the aprotic polar solvent. An average of the hourly yields of 2-furaldehyde in the reaction time between 0.5 and 5.5 hours is shown in Table 3.

Example 29

A procedure was performed in the same manner as in Example 2 except that 50.0 g of dimethyl sulfone (manufactured by Tokyo Chemical Industry Co., Ltd.) was used as the aprotic polar solvent. An average of the hourly yields of 2-furaldehyde in the reaction time between 0.5 and 5.5 hours is shown in Table 3.

TABLE 3

| Catalyst | Solvent | FAL yield (mol %) (average in 0.5-5.5 h) | Temperature of reaction mixture (average in 0.5-5.5 h) |
| --- | --- | --- | --- |
| Example 28 | Aluminum sulfate 14-18 hydrate | Phthalide | 15.4 | 224° C. |
| Example 29 | Aluminum sulfate 14-18 hydrate | Dimethyl sulfone | 24.7 | 222° C. |

Example 30

<Production of 2-Furaldehyde from Glucose>

2-Furaldehyde was produced from glucose by performing a reaction in the same manner as in Example 1 except that 2.0 g of the B—P composite oxide prepared in Example 3 was used as the solid acid catalyst, and a 25% by weight aqueous solution of glucose was used in place of the slurry (containing cellulose at 25% by weight) prepared by mixing cellulose and desalted water.

An average of the hourly yields of 2-furaldehyde in the reaction time between 0.5 and 5.5 hours in the above reaction is shown in Table 4.

Example 31

A procedure was performed in the same manner as in Example 30 except that the temperature of the oil bath during the reaction was set to 210° C. An average of the hourly yields of 2-furaldehyde in the reaction time between 0.5 and 5.5 hours is shown in Table 4.

Example 32

A procedure was performed in the same manner as in Example 30 except that the temperature of the oil bath during the reaction was set to 250° C. An average of the hourly yields of 2-furaldehyde in the reaction time between 0.5 and 5.5 hours is shown in Table 4.

Example 33

A procedure was performed in the same manner as in Example 30 except that a 25% by weight aqueous solution of fructose was used in place of the 25% by weight aqueous solution of glucose. An average of the hourly yields of 2-furaldehyde in the reaction time between 0.5 and 5.5 hours is shown in Table 4.

Example 34

A procedure was performed in the same manner as in Example 30 except that a 25% by weight aqueous solution of sucrose was used in place of the 25% by weight aqueous solution of glucose. An average of the hourly yields of 2-furaldehyde in the reaction time between 0.5 and 5.5 hours is shown in Table 4.

TABLE 4

| | Catalyst | Reaction substrate | FAL yield (mol %) (average in 0.5-5.5 h) | Temperature of reaction mixture (average in 0.5-5.5 h) |
|---|---|---|---|---|
| Example 30 | B—P composite oxide | Glucose | 31.7 | 226° C. |
| Example 31 | B—P composite oxide | Glucose | 28.3 | 205° C. |
| Example 32 | B—P composite oxide | Glucose | 24.6 | 245° C. |
| Example 33 | B—P composite oxide | Fructose | 29.5 | 226° C. |
| Example 34 | B—P composite oxide | Sucrose | 32.1 | 225° C. |

Example 35

To a 100-mil four-necked flask in which a Teflon (registered trademark) stirring bar was placed, a Teflon (registered trademark)-coated thermocouple (for measuring the temperature of the reaction mixture), a Claisen connecting tube and a Liebig condenser (for cooling a distillate liquid), a 50-ml Erlenmeyer flask (a sampling receiver (containing 30 ml of tetrahydrofuran (manufactured by Junsei Chemical Co., Ltd., special grade) as a solvent for trapping the distillate and 0.5 ml of diethylene glycol diethyl ether (manufactured by Kishida Chemical Co., Ltd., special grade) as an internal standard material for gas chromatography analysis)) were fitted. A tape heater was wound around the portion of the Claisen connecting tube, and the tape heater was covered with a heat insulating material made of silicone rubber. Nitrogen was allowed to flow through the reactor at 20 ml/min so that the atmosphere in the reactor was brought into a nitrogen atmosphere. Thereafter, 5.0 g of corn starch (manufactured by Kishida Chemical Co., Ltd., first class grade), 50.0 g of sulfolane (manufactured by Kishida Chemical Co., Ltd., special grade) as the aprotic polar solvent, and 2.0 g of a B—P composite oxide (prepared in Example 3) as the solid acid catalyst were added thereto and mixed by stirring. The temperature of an oil bath was raised to 230° C. over 40 minutes using a program temperature controller and maintained as such. The heating of the tape heater (the temperature of the outer surface of the Claisen connecting tube was set to 120° C.) was initiated simultaneously with the initiation of raising of the temperature of the oil bath. When the internal temperature of the flask reached 110° C., desalted water was supplied at a supply rate of 6.0 g/hour. The reaction initiation time was defined as the time 10 minutes after the temperature of the oil bath reached 230° C., and the sampling receiver was replaced hourly (−1.0 hours, 1.0-2.0 hours, 2.0-3.0 hours, and 3.0-4.0 hours) to collect the receiver containing the distillate liquid. The collected receiver was shaken to stir the contents well, and the production amount of 2-furaldehyde was determined by gas chromatography analysis (an internal standard method) in the same manner as in Example 1. Incidentally, the FAL yield was calculated according to the following formula on the basis of the weight of the fed raw material.

FAL yield(wt %)=weight of produced FAL(analytical value of gas chromatography)/weight of fed starch×100

The results are shown in Table 5.

Example 36

A procedure was performed in the same manner as in Example 35 except that 5.0 g of disposable chopstick chips (chips with a size of 4 to 7 mm obtained from disposable chopsticks made of aspen wood) was used in place of the corn starch. The FAL yield was calculated according to the following formula.

FAL yield(wt %)=weight of produced FAL(analytical value of gas chromatography)/weight of fed disposable chopstick chips×100

The results are shown in Table 5.

TABLE 5

| | | | FAL yield | | Temperature of |
|---|---|---|---|---|---|
| | Catalyst/reaction substrate | Reaction time | (wt %) | (Integrated value) | reaction mixture |
| Example 35 | B—P composite oxide 2.0 g | −1.0 h | 13.6 | 13.6 | 227° C. |
| | Corn starch 5.0 g | 1.0 h-2.0 h | 1.3 | 14.9 | 226° C. |
| | | 2.0 h-3.0 h | 0.1 | 15.0 | 227° C. |
| | | 3.0 h-4.0 h | 0.0 | 15.0 | 227° C. |

TABLE 5-continued

|  | Catalyst/reaction substrate | Reaction time | FAL yield (wt %) | FAL yield (Integrated value) | Temperature of reaction mixture |
|---|---|---|---|---|---|
| Example 36 | B—P composite oxide 2.0 g | -1.0 h | 1.7 | 1.7 | 226° C. |
|  | Disposable chopstick chips | 1.0 h-2.0 h | 4.1 | 5.8 | 226° C. |
|  | 5.0 g | 2.0 h-3.0 h | 3.0 | 8.8 | 226° C. |
|  |  | 3.0 h-4.0 h | 1.1 | 10.0 | 227° C. |

Example 37

3.02 g of boric acid was dissolved in a mixed solution of 300 ml of desalted water and 30 ml of isopropanol, and while stirring the resulting solution, 33.25 g of aluminum isopropoxide was added thereto. The resulting mixture was stirred as such for 3 hours, and then left overnight. Subsequently, the mixture was heated to 80° C. for 1 hour, and further heated to 90° C. for 1 hour, thereby concentrating the mixture to a volume of about 100 ml, followed by evaporation to dryness on an evaporating dish. The obtained solid was calcined at 550° C. for 2 hours in an air stream, whereby an Al—B composite oxide was obtained (feed composition: Al/B=1.0/0.3 (molar ratio)).

A reaction was performed at an oil bath temperature of 230° C. and a reaction mixture temperature of 223 to 224° C. in the same manner as in Example 1 except that 2.0 g of the above Al—B composite oxide was used as the solid acid catalyst. The yield of furaldehyde in 1 hour during the reaction time between 3.5 and 4.5 hours was 40.8%, and the yield of furaldehyde in 1 hour during the reaction time between 4.5 and 5.5 hours was 43.3%.

Example 38

A reaction was performed at an oil bath temperature of 230° C. and a reaction mixture temperature of 220 to 222° C. in the same manner as in Example 1 except that the solid acid catalyst was not fed to a 100-ml four-necked flask, and as the solid acid catalyst which was not dissolved in the aprotic polar solvent, a 1.0% by weight aqueous solution in which aluminum sulfate 14-18 hydrate (Kishida Chemical Co., Ltd., special grade) was dissolved in desalted water was supplied at a rate of 2.0 g/hour separately from the cellulose slurry. An average of the hourly yields of furaldehyde in the reaction time between 0.5 and 5.5 hours was 27.1%.

While the present invention has been described in detail with reference to particular embodiments, it would be obvious to those skilled in the art that various changes and modifications can be made without departing from the spirit and scope of the invention. The present application is based on Japanese Patent Application No. 2011-016943 filed on Jan. 28, 2011, the contents of which are incorporated herein as reference.

INDUSTRIAL APPLICABILITY

The method for producing 2-furaldehyde of the invention is advantageous in that 2-furaldehyde can be obtained from a sugar raw material containing a hexose as a constituent component such as cellulose with an economically satisfactory good yield while suppressing the corrosion of a reactor, reducing a waste acid, and suppressing a decrease in the activity of a catalyst observed in an acid catalyst.

The invention claimed is:

1. A method for producing 2-furaldehyde, comprising heating, in a reaction system, a sugar raw material comprising a hexose as a constituent component in an aprotic polar solvent in the presence of a solid acid catalyst,
    wherein the solid acid catalyst is at least one selected from the group consisting of aluminum sulfate, zirconium sulfate, zinc sulfate, nickel sulfate, ferric sulfate, ferrous sulfate, copper sulfate, magnesium sulfate, cobalt sulfate, and a rare earth sulfate; and
    the aprotic polar solvent is at least one selected from the group consisting of sulfolane, dimethyl sulfone and phthalide.

2. The method according to claim 1, further comprising separating the produced 2-furaldehyde from the solvent or byproducts and the solid acid catalyst remaining in the reaction system, while distilling away the produced 2-furaldehyde to the outside of the reaction system.

3. The method according to claim 1, wherein the solid acid catalyst is a metal sulfate which is not uniformly dissolved in the aprotic polar solvent.

4. The method according to claim 1, wherein the catalyst is uniformly dissolved or in a uniform liquid prior to reaction, and is in a solid state during the reaction.

5. The method according to claim 1, wherein the 2-furaldehyde is produced from a hexose component of a sugar raw material comprising a hexose as a constituent component.

6. The method according to claim 1, wherein the solid acid catalyst is a hydrate.

7. The method according to claim 1, further comprising supplying water to the reaction system.

8. The method according to claim 1, further comprising:
    collecting the solid acid catalyst with other insoluble components from a reaction mixture after the heating; and then
    collecting the solid acid catalyst by dissolving the solid acid catalyst in a solvent to separate the solid acid catalyst from the insoluble components.

9. The method according to claim 8, wherein the collected solid acid catalyst is recycled into the reaction system.

10. The method according to claim 1, wherein the 2-furaldehyde is produced without production of hydroxymethylfurfural.

11. The method of claim 1,
    wherein at least one of the solid acid catalyst, the sugar raw material, and the aprotic polar solvent is separately supplied to the reaction system.

* * * * *